United States Patent
Schmieding

(10) Patent No.: US 7,959,636 B2
(45) Date of Patent: Jun. 14, 2011

(54) OSTEOCHONDRAL REPAIR USING PLUG FASHIONED FROM WHOLE DISTAL FEMUR OR CONDYLE FORMED OF HYDROGEL COMPOSITION

(75) Inventor: Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1952 days.

(21) Appl. No.: 10/638,489

(22) Filed: Aug. 12, 2003

(65) Prior Publication Data

US 2004/0034437 A1     Feb. 19, 2004

Related U.S. Application Data

(60) Provisional application No. 60/403,472, filed on Aug. 15, 2002.

(51) Int. Cl.
*A61F 2/46* (2006.01)

(52) U.S. Cl. ..................................................... 606/86 R

(58) Field of Classification Search .................. 606/79, 606/82, 83, 84, 86, 87, 88, 89; 623/16.11, 623/23.56, 23.67, 23.6, 23.61, 23.63, 14.12
See application file for complete search history.

(56) References Cited

U.S. PATENT DOCUMENTS

| | | | |
|---|---|---|---|
| 5,919,196 A * | 7/1999 | Bobic et al. | 606/86 |
| 5,981,826 A * | 11/1999 | Ku et al. | 623/23.72 |
| 6,005,161 A * | 12/1999 | Brekke et al. | 424/422 |
| 6,077,987 A * | 6/2000 | Breitbart et al. | 623/23.72 |
| 6,083,522 A * | 7/2000 | Chu et al. | 424/423 |
| 6,398,816 B1 * | 6/2002 | Breitbart et al. | 623/23.72 |
| 6,440,141 B1 * | 8/2002 | Philippon | 606/99 |
| 6,488,033 B1 * | 12/2002 | Cerundolo | 128/898 |
| 6,592,588 B1 * | 7/2003 | Bobic et al. | 606/79 |
| 6,595,998 B2 * | 7/2003 | Johnson et al. | 606/90 |
| 6,626,945 B2 * | 9/2003 | Simon et al. | 623/17.19 |
| 6,632,246 B1 * | 10/2003 | Simon et al. | 623/14.12 |
| 7,008,635 B1 * | 3/2006 | Coury et al. | 424/426 |
| 7,049,348 B2 * | 5/2006 | Evans et al. | 521/82 |
| 7,166,133 B2 * | 1/2007 | Evans et al. | 623/23.51 |

* cited by examiner

*Primary Examiner* — Anu Ramana

(74) *Attorney, Agent, or Firm* — Dickstein Shapiro LLP

(57) ABSTRACT

A method and apparatus for repairing isolated chondral defects using synthetic implants. Lesions in articular tissue are corrected by forming a recipient socket in the tissue. A donor graft of a size corresponding to the recipient socket is harvested from a synthetic specimen made of a synthetic tissue material, such as poly (vinyl) alcohol hydrogel. The donor graft is implanted into the recipient socket.

9 Claims, 6 Drawing Sheets

OSTEOCHONDRAL REPAIR USING PLUG FASHIONED FROM WHOLE DISTAL FEMUR OR CONDYLE FORMED OF HYDROGEL COMPOSITION

The present application claims the benefit of U.S. provisional application No. 60/403,472, filed Aug. 15, 2002, the disclosure of which is incorporated herein by reference.

BACKGROUND OF THE INVENTION

1. Field of the Invention

The present invention relates to the surgical treatment of isolated articular chondral defects and, more specifically, to methods and instruments for replacement of articular cartilage in the knee using grafts harvested from a synthetic tissue specimen.

2. Description of the Related Art

Methods and apparatus for surgical treatment of isolated articular chondral defects by autograft and allograft transplantation are known. See, for example, U.S. Pat. Nos. 5,919,196, 6,591,581, and 6,592,588, having common assignment with the present application.

Various synthetic biomaterials are known. One of these, Salubria™, is an elastic biomaterial sold by Salumedica of Atlanta, Ga. Salubria™ is a poly (vinyl) alcohol hydrogel composition which is similar to human tissue in its mechanical and physical properties. See U.S. Pat. Nos. 5,981,826; 6,231,605; and published Application No. U.S. 2001/0029399, the disclosures of which are incorporated herein by reference.

The Salubria™ organic polymer-based material is highly biocompatible and hydrophilic (water loving); it contains water in similar proportions to human tissue. Although Salubria is soft and compliant like human tissue, it has proven to be exceptionally wear resistant and strong, making it an ideal implant material.

Salubria™ can withstand millions of loading cycles, yet it is soft enough to match the compliance of normal biological tissue. These properties allow Salubria™ to be molded into anatomic shapes and sterilized, making it usefuil for orthopedic applications.

It would be advantageous to have methods and systems for utilizing synthetic grafts in the repair of isolated chondral defects.

SUMMARY OF THE INVENTION

The present invention provides methods and apparatus for repair of isolated chondral defects using a synthetic substance, preferably a synthetic osteochondral graft material, such as Salubria™. The procedure can be utilized, for example, to anatomically re-establish a structural load-bearing surface to a damaged load bearing surface of the femoral condyle using implants harvested from synthetic anatomical specimens. Partial and full-thickness osteochondral lesions, 1.5-3.5 centimeters in diameter, are particularly amenable to treatment according to the methods of the present invention.

DETAILED DESCRIPTION OF THE PREFERRED EMBODIMENTS

In the present invention, a synthetic tissue specimen, such as an entire artificial distal femur, condyle, or hemi-condyle is created from synthetic biomaterial, such as Salubria™, and is delivered to a surgeon along with a set of surgical socket-forming and donor graft harvesting instrumentation. The tissue specimen is formed to closely approximate the anatomical tissue being repaired. The surgeon uses the instrumentation to fashion donor graft from the tissue specimen for osteochondral repair. The procedure is described below, with reference to the accompanying drawings.

Figure 1:
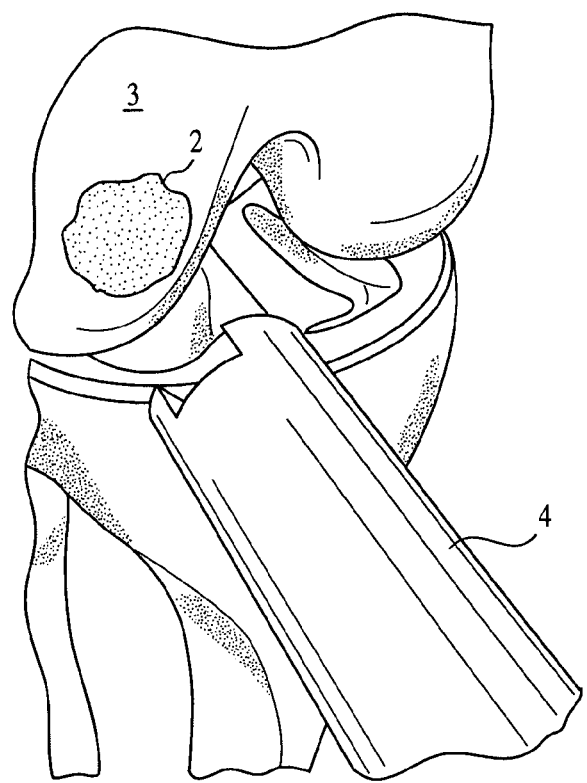
FIG. 1 illustrates a surgical step of sizing a lesion according to the present invention.

Referring first to FIG. 1, following standard pre-operative examination and diagnostic studies confirming the size and extent of the lesion 2 on an articular surface of femoral condyle 3, a standard para-patellar arthrotomy is carried out to expose the defect. Cannulated sizers 4 in various diameters are selected to estimate and approximate coverage of the lesion 2. Sizers 4 preferably are provided in 15, 18, 20, 25, 30, and 35 mm sizes.

Figure 2:
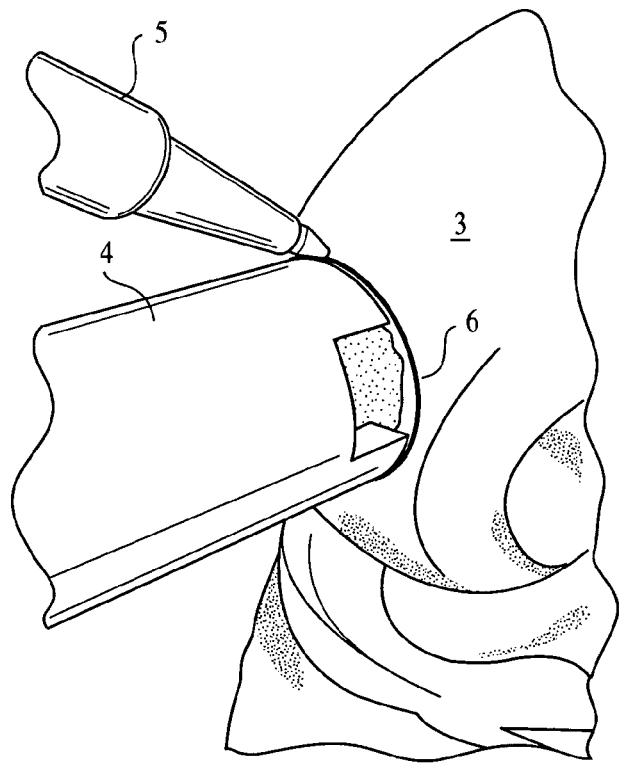
FIG. 2 illustrates a surgical step of marking an articular surface according to the present invention.
Figure 3:
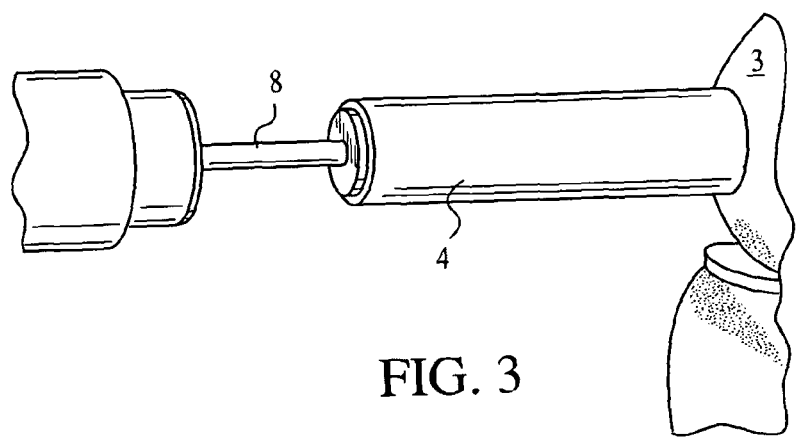
FIG. 3 illustrates a surgical step of drilling a guide pin into bone according to the present invention.

Referring to FIG. 2, once the appropriate size for the recipient socket is determined, a marker 5 is used to form a circumferential mark 6 on the condyle 3 around the cylinder of sizer 4. As shown in FIG. 3, a guide pin 8 is drilled through the sizer 4 past the lesion 2 and into bone. The sizer 4 is removed and a reference mark 10 is placed in a superior 12:00 o'clock position. See FIG. 3.

Figure 4:
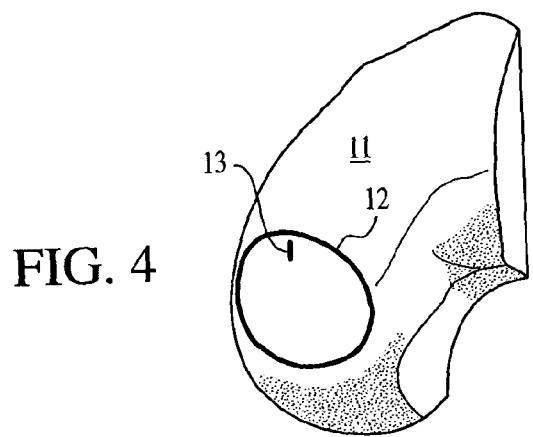
FIG. 4 illustrates a surgical step of marking a synthetic hemi-condyle according to the present invention.

Referring to FIG. 4, markings are placed on a synthetic hemi-condyle 11 using the sizer 4 which was previously utilized to establish the recipient defect size and mark the condyle 3. The sizer 4 is placed over the synthetic hemi-condyle 11 and is used to circumferentially mark 12 the surface of the hemi-condyle 11 in an area corresponding to that of the lesion 2 on the damaged articular surface of condyle 3. The sizer is removed and a reference mark 13 is placed in a superior 12:00 o'clock position on the inside of the circle mark 12 on the hemi-condyle 11.

Figure 5:
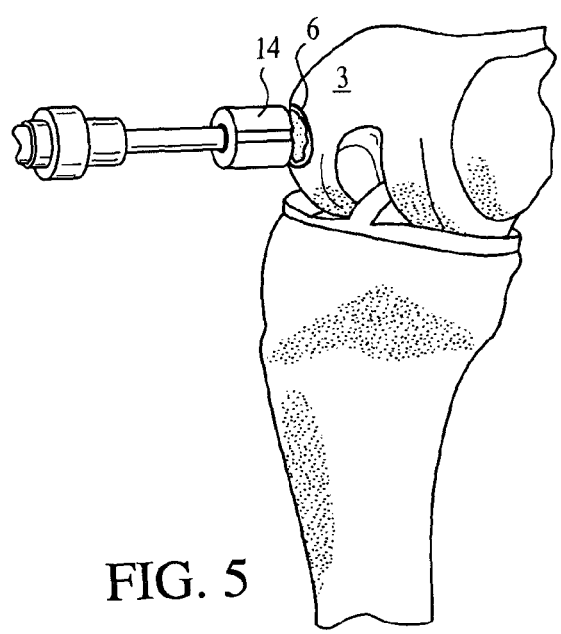
FIG. 5 illustrates a surgical step of scoring peripheral cartilage according to the present invention.

Referring to FIG. 5, the sizer is replaced with an appropriately sized recipient harvester 14. The peripheral cartilage on the condylar surface is scored to the underlying subchondral bone. Scoring the peripheral cartilage obviates ancillary damage to the undamaged, peripheral articular surface. The harvester 14 is removed, leaving the guide pin 8 in place.

Figure 6:
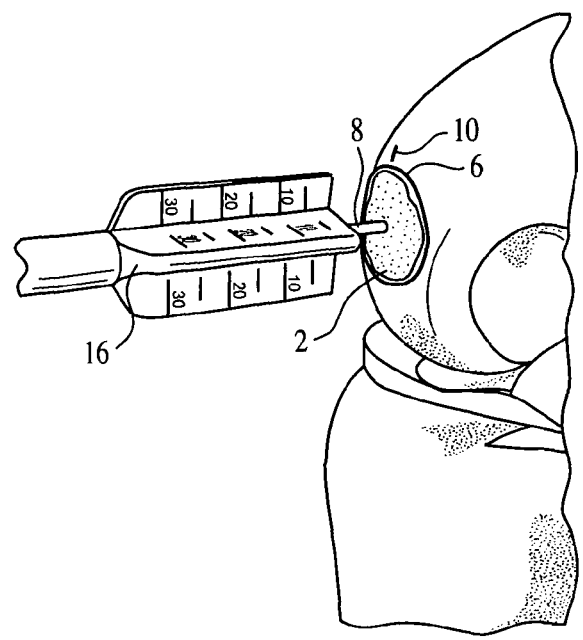
FIG. 6 illustrates a surgical step of boring into bone to form a recipient socket site according to the present invention.

Referring to FIG. 6, a cannulated calibrated recipient counterbore 16 is secured to the drill and placed over the drill pin 8. Recipient socket 17 (FIG. 9) is drilled into the lesion 2 and subchondral bone to a depth of 8 to 10 mm. Bleeding subchondral surfaces should be confirmed.

Figure 7:
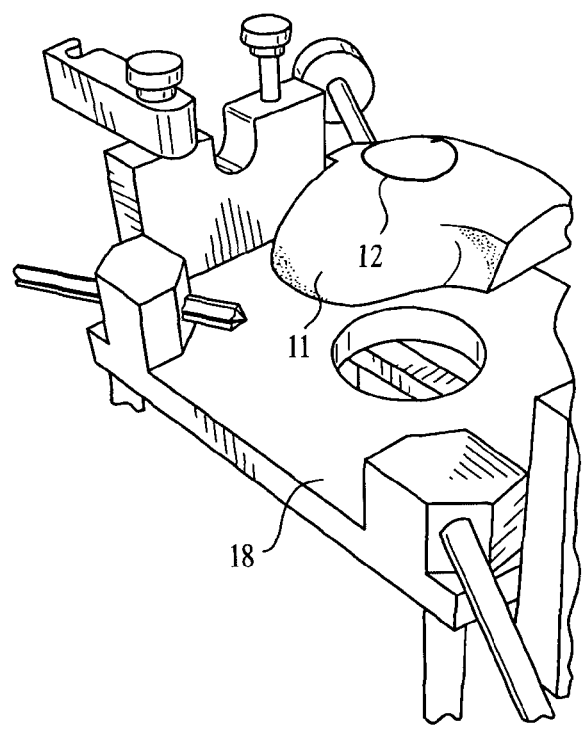
FIG. 7 illustrates a surgical step of securing the synthetic hemi-condyle in a workstation according to the present invention.
Figure 8:
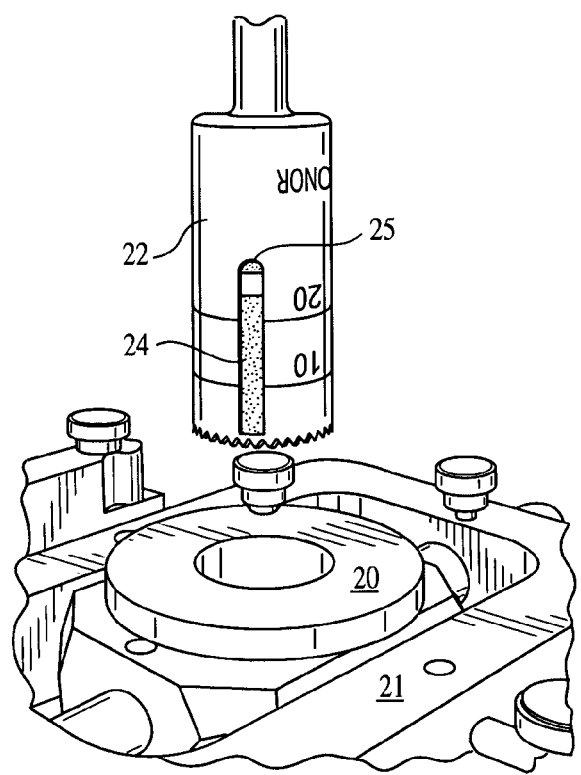
FIG. 8 illustrates a surgical step of harvesting a core from the synthetic hemi-condyle secured in the workstation according to the present invention.

Preparation of the donor graft is described with reference to FIGS. 7-10. Referring to FIG. 7, donor condyle 11 is secured in a workstation 18. As shown in FIG. 8, a workstation bushing 20 of corresponding size is placed into a top housing 21 over the donor hemi-condyle 11 and set to the exact angle necessary to match the recipient's contour. The housing 21 is fastened securely.

A calibrated donor harvester 22 is connected to a drill and passed through the bushing 20 into the proximal graft housing 21 and rested upon the surface of the donor condyle 11. The harvester 22 is drilled through the entirety of the donor hemi-condyle 11. The harvester 22 is removed from the graft housing, securely holding the corresponding cylindrical donor graft core 24, which can be visualized through slot 25. Donor graft 24 is extracted gently from the harvester 22 so as not to disturb the articular surface or underlying subchondral bone.

Figure 9:
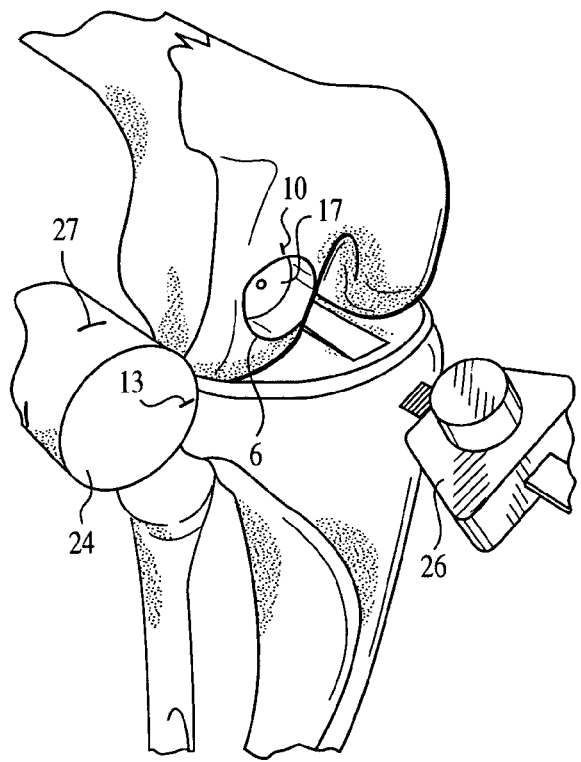
FIG. 9 illustrates a surgical step of transferring depth measurements to the core according to the present invention.

Referring to FIG. 9, a depth measurement guide 26 is used to measure the recipient depth in four quadrants: north, south, east and west. The depth measurements. are transferred to the synthetic graft core 24, which is appropriately measured and marked 27 by referencing the four quadrant depths recorded from the recipient socket 17 that was created.

Figure 10:
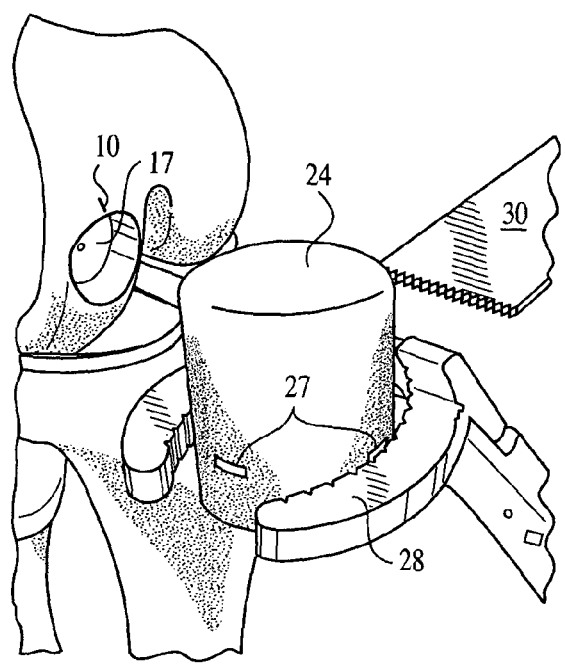
FIG. 10 illustrates a surgical step of cutting the harvested core to length according to the present invention.

Referring to FIG. 10, the donor graft 24 is secured in holding forceps 28 and trimmed by a reciprocating saw 30 to achieve the appropriate press fit accommodation of the recipient socket depth. The donor graft 24 is positioned with the articular surface inferior to cut.

Figure 11:
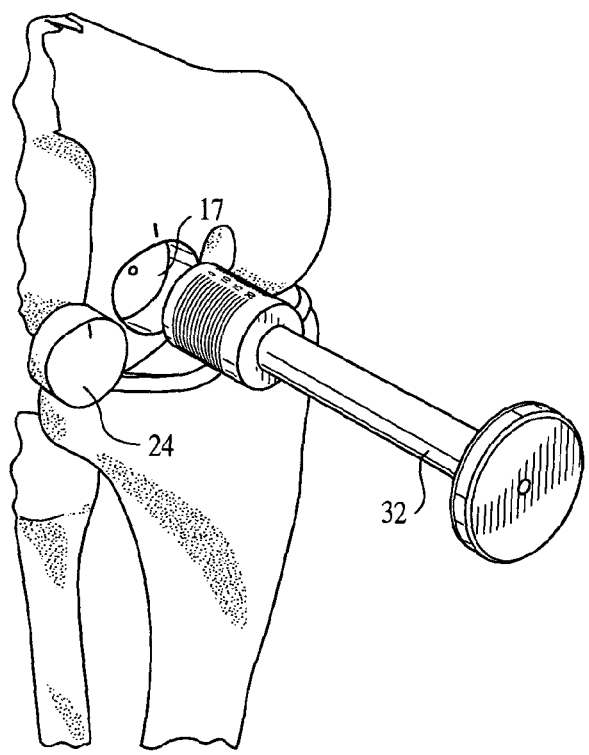
FIG. 11 illustrates a surgical step of dilating the recipient socket site according to the present invention.

Referring to FIG. 11, a calibrated dilator 32 is inserted into the recipient socket site 17 to achieve a one half mm socket dilation. The end of the dilator is lightly tapped with a mallet. Dilation will also smooth the recipient socket surfaces.

Figure 12:
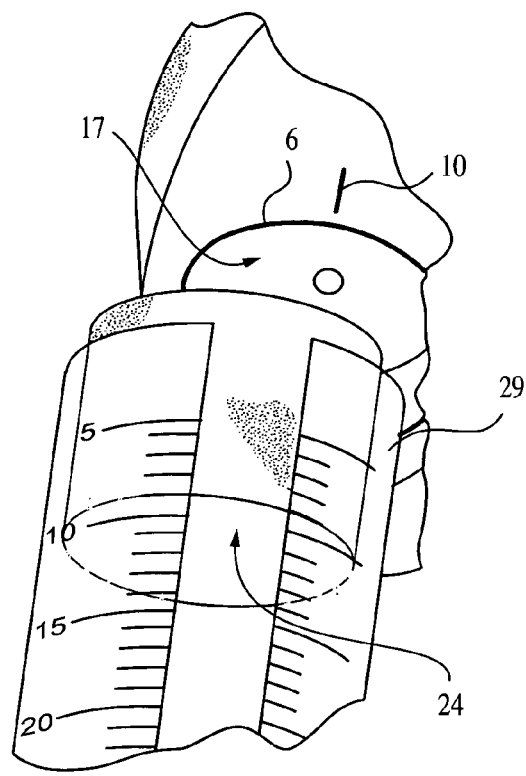
FIG. 12. illustrates a surgical step of placement of the harvested core into the recipient socket using a delivery tube according to the present invention.
Figure 13:
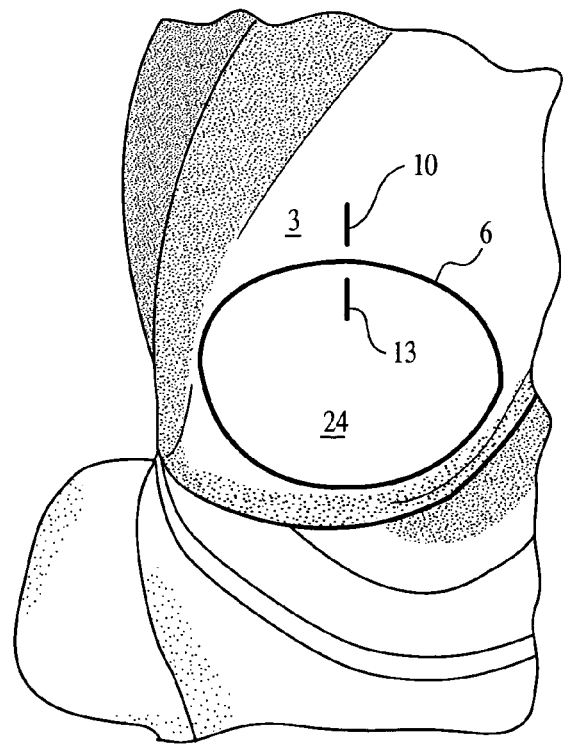
FIG. 13 illustrates a complete core implant according to the present invention.

Referring to FIG. 12, once the precise depth of the donor plug (matching the recipient socket) is obtained, the donor plug 24 is line to line fitted with reference to the marks 10 and 13 into the recipient socket. Cancellous graft is inserted into the bed prior to insertion of the donor plug, if necessary. The donor graft 24 is inserted into a slotted, transparent, calibrated delivery tube 29 for insertion into the recipient socket 17. A tamp corresponding to the graft's size is positioned against the plug. Gentle taps are recommended for seating the graft 24 into the socket 17. Referring to FIG. 13, the plug 24 is implanted until all edges are flush with the surrounding cartilage rim.

In situations necessary for plug removal, a graft retriever may be secured into the plug to facilitate extraction. At the conclusion of the procedure, the wound is closed in a routine fashion. Sterile dressing and a protective brace are applied during the initial wound-healing phase. Ambulation with the use of crutches and weight-bearing allowances are determined based on the size and the extent of the weight-bearing lesion reconstructed.

Although the present invention has been described in connection with preferred embodiments, many modifications and variations will become apparent to those skilled in the art.

What is claimed as new and desired to be protected by Letters Patent of the United States is:

1. A method of repairing isolated chondral defects, comprising:
    providing a donor hemi-condyle comprising a synthetic specimen in the shape of a hemi-condyle, the synthetic specimen being formed of a poly (vinyl) alcohol hydrogel;
    forming a recipient socket in a lesion area of a lesion on a damaged, load bearing surface of a femoral condyle;
    harvesting a donor graft in the form of a plug corresponding in shape to the recipient socket formed in the femoral condyle from an area of the donor hemi-condyle corresponding to the lesion area of the femoral condyle, by securing the donor hemi-condyle in a workstation and cutting the donor graft from the donor hemi-condyle using a harvester; and
    implanting the donor graft in the recipient socket to anatomically re-establish the load bearing surface of the femoral condyle, the donor graft being capable of withstanding loading cycles of the femoral condyle.

2. A method according to claim 1, wherein the recipient socket is formed in an articular surface.

3. A method according to claim 2, wherein the socket is formed by scoring peripheral cartilage on the articular surface to underlying subchondral bone, and boring a counterbore in the subchondral bone.

4. A method according to claim 3, further comprising dilating the recipient socket.

5. A method according to claim 1, wherein the step of forming a recipient socket includes determining a size of a lesion to be repaired.

6. A method according to claim 5, further comprising marking the size of the lesion on a surface of the anatomical tissue, and providing a reference mark on the surface.

7. A method according to claim 6, further comprising providing a corresponding reference mark on a surface of the donor graft.

8. A method according to claim 1, wherein implanting the donor graft in the recipient socket includes aligning reference marks formed at the recipient socket and on the donor graft, and impacting the donor graft into the recipient socket.

9. A method according to claim 1, further comprising cutting the donor graft to achieve a length equal to a depth of the recipient socket.

\* \* \* \* \*